United States Patent [19]

Hickey

[11] Patent Number: 5,436,220
[45] Date of Patent: Jul. 25, 1995

[54] COTTON CANOPY CONDITIONER TO PREVENT COTTON REGROWTH COMPRISING GLYPHOSATE OR SULFOSATE AND A KREBS CYCLE ACID

[75] Inventor: Joseph A. Hickey, Lakeland, Fla.

[73] Assignee: Micro Flo Company, Mulberry, Fla.

[21] Appl. No.: 216,339

[22] Filed: Mar. 23, 1994

[51] Int. Cl.⁶ ............................................. A01N 57/04
[52] U.S. Cl. ................................... 504/127; 504/128; 504/175; 504/206
[58] Field of Search ................ 504/127, 206, 128, 175

[56] References Cited

U.S. PATENT DOCUMENTS 4,436,547  3/1984  Sampson ................................. 71/76
4,999,041  3/1991  Grossmann et al. ..................... 71/70
5,186,733  2/1993  Broadhurst et al. ................. 504/195
5,352,264  10/1994  Medina Vega ......................... 71/23

Primary Examiner—S. Mark Clardy
Attorney, Agent, or Firm—Banner & Allegretti, Ltd.

[57] ABSTRACT

A conditioner containing a regrowth inhibitor containing glyphosate, sulfosate, or a salt of either is used at 0–50% open boll to condition cotton plants before chemical defoliation to prevent vegetative regrowth after defoliation. The conditioner can also contain at least one of the Krebs cycle acids, preferably an acid-containing extract from pentosan-containing seed hulls, to increase yields of high quality fibers and vigorous seeds.

12 Claims, No Drawings

COTTON CANOPY CONDITIONER TO PREVENT COTTON REGROWTH COMPRISING GLYPHOSATE OR SULFOSATE AND A KREBS CYCLE ACID

FIELD OF THE INVENTION

The invention relates to a composition and method of using the composition to condition cotton foliage for later application of a defoliant.

BACKGROUND OF THE INVENTION

There are two primary methods for harvesting a cotton crop. The first is by spindle picking where only relatively mature cotton (e.g., at least 60% open boll) is harvested in one or more pickings. Because cotton fibers are generally best at full maturity, spindle picking may harvest some fibers before they have achieved the desired fineness and length. The second is by strip picking where everything is stripped from the plant in a single picking. Strip picking occurs at 100% open boll, i.e., all bolls on the plants in a field are open. Fiber properties are generally at their peak at 100% open boll if only they can be harvested without reducing the crop value.

The presence of leaves on the cotton plants is a major source of crop value reduction. Both spindle and strip picking require that the cotton plants be free of leaves and other vegetative matter at the time of picking. The presence of green leaves can stain the cotton fibers and significantly reduce the crop value since cotton fibers are more difficult if not impossible to dye once stained by chlorophyll. The value of a cotton crop can be reduced as much as 5–10% by staining.

In addition to staining, because its is difficult to avoid harvesting leaves by the strip picking method. A precleaner separation stage can remove most of the burrs and many, but not all, of the leaves. If leaves or pieces thereof enter the gin, the leaves are broken down into very fine pieces that become mixed with the cotton fibers. Even 1 wt % of such vegetative fines may reduce the crop value by as much as 50%. Higher levels make the crop valueless.

The market has responded to the concerns over vegetative contamination of cotton with a variety of harvest aids. There are products available for defoliating cotton plants, enhancing the effects of defoliants, surfactants for assuring adequate contact, and boll openers for accelerating the maturation rate of cotton bolls.

Harvest aids are generally applied as a mixture about two weeks before the cotton is planned to be picked. This two week period may require some careful coordination because some cotton fields may take six weeks to harvest and, depending on the type of picking method used, may require two passes to complete the harvest. Unexpected events, rain or other weather delays, or a lack of adequate planning for the harvest may permit the cotton plants to begin to grow new vegetative matter as well as produce immature squares.

Fruiting sites in cotton are referred to as "squares." Each fruit bearing branch will form three fruiting sites ("squares") with approximately six days between square formations on each branch. New squares and the beginning of reproductive growth in cotton plants are referred to as "pinhead" squares due to their barely visible size. After about three days, the square has grown to about the size of a match head and is a period in the plant cycle referred to as a "match head square." The match head square continues to grow to about the size of an average adult fingernail before blooming ("early bloom"). Three days later, a boll has formed beneath the bloom. Roughly thirty days after early bloom, the product boll is fully mature and ready for harvest.

Regrowth and the production of immature squares pose a problem in effective harvesting and crop management. Regrowth is young, vital vegetative matter that cannot be effectively treated with defoliants. The tissue is too vigorous to succumb to the chemical effects. The conventional method for responding to regrowth is to apply a desiccant (to avoid fiber staining) and pick the cotton despite the dry vegetation accumulated with the cotton. The immature squares are also where weevils overwinter to infest the next crop and reduce its yield.

It would be desirable to have a way of preventing cotton plant regrowth after defoliation that did not materially affect yield or cotton fiber quality.

It would also be desirable to have a means for preventing the development of immature squares to reduce weevil infestation by eliminating sites for overwintering.

In some planting practices, cotton seeds from the harvested cotton are recovered and used for the next crop. It is desirable, therefore, that any treatment to deter regrowth not adversely affect the vigor of seeds from the treated plants.

SUMMARY OF THE INVENTION

It is an object of the invention to provide a composition and method of use thereof that controls cotton plant leaf regrowth following treatment with a defoliant.

It is also an objective of the invention to provide a composition and method for preventing the growth of squares in cotton plants after treatment thereof with a chemical defoliant.

In accordance with this and other objectives of the invention that will become apparent from the description herein is a process for preventing regrowth in cotton by applying to the cotton plant foliage a conditioner comprising glyphosate, sulfosate, or salts of either glyphosate or sulfosate in a sublethal amount sufficient to suppress vegetative regrowth after the conditioned plant is chemically defoliated.

In another aspect of the invention, seed vigor and lint quality as well as vegetative regrowth are maintained if the cotton plant is treated with the conditioner and at least one acid of the Krebs tricarboxylic acid cycle in an amount within the range of about 1–10,000 grams per hectare (g/ha). A preferred source for the Krebs acid is an extract from pentose-containing seed hulls that contains a mixture of tricarboxylic acids in conjunction with their associated carbohydrates.

The present invention provides a method and composition for increasing the economic value of cotton crops by reducing or eliminating the vegetative regrowth on the cotton plant after chemical defoliation. The reduction or elimination in vegetative regrowth is particularly valuable for maintaining the quality of the cotton and the yield despite the need for a second picking, unforeseen events that prohibit timely picking, or errors in harvest planning.

DETAILED DESCRIPTION

The invention relates to a conditioner containing a regrowth inhibitor that is applied either alone or in combination with at least one acid from the Krebs tricarboxylic acid cycle to condition the plant against regrowth and square formation following chemical defoliation. The conditioner according to the invention is applied at a time in the cotton growth cycle within the range from 0–50% open boll, preferably at a time within the range from about 10–50% open boll, even more preferably at a time within the range from about 30–50% open boll. Particularly good results are seen when the conditioner is applied at about 40% open boll.

Despite some minor loss in cotton yield that might be seen at the high conditioner application rates, the overall economic value of the crop is higher due to the absence of vegetative regrowth than if regrowth had occurred.

Regrowth inhibitors according to the invention are glyphosate, sulfosate, or agriculturally acceptable salts thereof. Glyphosate is a well known chemical sold commercially under the name ROUNDUP ® by the Monsanto Chemical Co., St. Louis, Mo. and widely used to kill plants.

For the present invention, glyphosate and the other regrowth inhibitors according to the invention are applied at a sublethal rate for cotton within the range of 5 g/ha to about 1000 g/ha, preferably 30–500 g/ha, and more preferably 50–300 g/ha. A highly preferred rate for application of regrowth inhibitor according to the invention is to use a rate of roughly ⅛ the rate needed to kill weeds. These sublethal rates condition the plant to exhibit reduced or no regrowth after treatment with a chemical defoliant between first and second cotton picking periods using the strip picking method.

A preferred second component for the conditioner according to the invention is at least one of the Krebs tricarboxylic acids. The Krebs tricarboxylic acids and metabolic precursors thereof are associated with the well known Krebs cycle for photosynthetic activity in plants. The acids and their metabolic precursors include: citric acid, cis-acotinic acid, isocitric, acetic, oxalosuccinic, $\alpha$-ketoglutaric acid, trihydroxyglutaric acid, succinic acid, fumaric acid, malic acid, oxaloacetic acid, pyruvic acid, lactic acid, glycolic acid, and 2,3,4-trihydroxypentanedioic acid. For the present invention, the acids may be used alone or, preferably, as a mixture of at least three of the acids.

Even more preferably, the Krebs acids are present in a complex mixture from the extraction of pentose-containing seed hulls where they are associated with the corresponding carbohydrate (triose, pentose, and hexose). Preferably, the seed hulls exhibit a hemicellulose membrane type from which it is easier to recover pentose products by extraction under alkali conditions or by hydrolysis with dilute mineral acids than other cellulosic membranes.

Seed hulls that can be used as a source for extraction include rice hulls, oat hulls, corn hulls, cotton hulls, and virtually any other pentose-containing hull, either alone or in combination. The hemicellulose of oat and rice bran hulls is of the glucoxylane type producing xyloses as the main hydrolysis product. A preferred material for the extraction is rice hulls.

Seed hull extract in accordance with the invention is prepared by a process comprising and preferably consisting essentially of: (a) contacting seed hulls with nitric acid (preferably in a concentration of 4–6 %) to hydrolyze pentosan polymers in said hulls to form a pentose-containing extract; (b) agitating said extract with steam (preferably at a temperature within the range of 75°–85° C. for 8–20 hours) to partially oxidize pentoses in the extract to a mixture of polyhydroxycarboxylic acids including at least one of the acids associated with the Krebs cycle; (c) separating the seed hull solids from the partially oxidized aqueous extract; (d) contacting the aqueous extract with additional nitric acid to oxidize the extract further into a dilute partially oxidized product stream containing 2,3,4-trihydroxypentanedioic acid; and (e) concentrating the dilute, partially oxidized, product (preferably by vacuum distillation at a temperature of no more than 60° C., preferably no more than 45° C.) to produce a concentrated product containing and preferably consisting essentially of at least one of the acids associated with the Krebs cycle, at least one of the carbohydrates related to the acids, and a variety of related polyhydroxycarboxylic acids that do not have a material, adverse effect on the product's ability to condition cotton plants for defoliation in accordance with the invention.

The result of the extraction process is a dilute product mixture that can be recognized by the properties described in Table 1.

TABLE 1

| | |
|---|---|
| Appearance and odor | Yellowish-clear solution having the odor of fermented glucose |
| Boiling Point | 107–109° C. at 760 mm Hg |
| Density | 1.020–1.040 g/cc at 20° C. |
| Trihydroxypentanedioic acid content | 2.5–3.5% |
| Nitric acid | Maximum of 1% |

Virtually any conventional method can be used to contact the seed hulls with the nitric acid. Although any extraction process can be used, exemplary batch methods include spray percolation, full immersion, and intermittent drainage of nitric acid through a bed of seed hull solids. Exemplary continuous contacting methods include multistage concurrent or countercurrent extraction sequences, moving bed 5percolation, tilting pan filters, and horizontal filters. The preferred contacting method is a batch, full immersion process in a pressurizable container. Some oxidation will occur during this initial extraction stage. The primary reaction is, however, extraction of the trioses, pentoses, and hexoses from the hull solids and is generally referred to herein as "the extraction stage."

After extraction, spent seed hull solids are separated from the extract solution. Separation avoids further reaction or extraction during the subsequent oxidation step which have a material, adverse effect on the basic and novel cotton foliage conditioning effects of the invention. The separation can be accomplished by any of the conventional liquid-solid separation processes including centrifugation, filtration, straining, sedimentation, decantation, and hydrocyclone separation either alone or in serial combination. The preferred separation method is decantation followed by centrifugal separation.

A hull extract containing a complex mixture of Krebs cycle acids including 2,3,4-trihydroxypentanedioic acid and the corresponding carbohydrates is commercially available from Micro Flo Company, Mulberry, Florida under the trademark PHCA ®. A 6:1 dilution thereof is also commercially available from Micro Flo Company under the trademark CENERGY ®. For purposes of calculation, total carboxylic acid content of such mixtures is expressed as the trihydroxypentanedioic acid content and is generally within the range of 4.5–5.5 wt % for PHCA ®.

The Krebs acid component is applied in admixture with the other conditioners at an application rate within the range from about 1–10,000 g Krebs acid/ha. Preferably, the acid component is applied at a rate within the range from about 10–1000 g/ha, more preferably within the range from about 50–500 g/ha based on an active Krebs acid concentration rate within the range of 3 wt %.

As a composition, the mixture of regrowth inhibitor to Krebs acid component should have a weight ratio of active ingredients within the range of regrowth inhibitor to Krebs acids from about 1:100 to about 100:1, preferably about 1:20.1 to about 20:1, and more preferably about 1:3 to about 3:1.

It should be noted that Sampson U.S. Pat. No. 4,436,547 describes the use of a Krebs acid for improving the action of an agricultural chemical applied simultaneously or closely in time. Specifically, Sampson suggests in column 1, lines 29–36 that:

"The additive acts in either of the following ways, viz., it modifies the way in which the organism takes up and/or moves or internally distributes the chemical, and/or it modifies the metabolism of the organism without affecting take-up or distribution of the chemical, thereby achieving the desired action or improvement in action of the agricultural chemical."

While not wishing to be bound by theory, the effect of the Krebs acid in the present invention is not explained by an improvement in the action of the glyphosate conditioner. Improved glyphosate action does not explain the improvements in lint quality or retained seed vigor exhibited with co-application of the Krebs acid component. Instead, it appears that the Krebs acid component is selectively mitigating the glyphosate effects on fruit production, i.e., cotton fiber and vigorous seeds, and redirecting the glyphosate effects to vegetation.

In addition, conditioning treatment according to the invention reduces the available food supply for overwintering weevils. The result is a reduced weevil infestation for the beginning of the next cotton crop.

After conditioning with the glyphosate alone or with the Krebs acid component, harvesting aids including a chemical defoliant are applied to the cotton foliage about 10–15 days after conditioning and about two weeks before the planned harvest. For spindle picking, the harvest aids are applied at roughly 60–70% open boll: Any of the conventional defoliants, defoliant aids, surfactants, and boll opening aids for cotton plants can be used at conventional rates suitable for each. Exemplary defoliants and harvest aids include the defoliants tribufos (DEF ®), merphos, arsenic acid, thidiazuron (DROPP ®); the defoliant enhancer endothall (ACCELERATE ®); and the boll opener ethefon (PREPP ®). The most common and preferred defoliant is a tank mix of about 0.1 lb/acre thidiazuron (DROPP ®), about 0.5–1 lb/acre tribufos (DEF ®) for defoliation, and a suitable boll opening aid such as ethefon (PREPP ®) at 800–1000 g/ha.

EXAMPLES

The following examples are presented to assist in understanding the invention. The following table 2 presents the applicable conversion rates between liquid measures and applied weight rates.

TABLE 2

| Liquid Rate | Weight Rate |
| --- | --- |
| 0.25 pints/acre ROUNDUP ® | 63.6 g Glyphosate/ha |
| 0.5 pints/acre ROUNDUP ® | 127.1 g Glyphosate/ha |
| 0.75 pints/acre ROUNDUP ® | 190.7 g Glyphosate/ha |
| 1.0 pints/acre ROUNDUP ® | 254.2 g Glyphosate/ha |
| 0.3 gallons/acre PHCA ® | 81.7 g Krebs acids/ha |

The harvest aids applied in the examples, unless otherwise identified, were a mixture of the defoliant DROPP ®(22.7 g AI/acre) and the boll opener PREP ®(908 g AI/acre). Aids were applied at 70% open boll.

Example 1

In this example, glyphosate was applied once or twice to Cultivar CAB-CS cotton plants at rates of 127.1–254.2 grams per hectare using 0.5–1.0 pints per acre of the commercially available formulation containing glyphosate, ROUNDUP ®. Table 3 lists the relevant dates for growth of the cotton plants used for this example.

TABLE 3

| Event Schedule | |
| --- | --- |
| Date of Planting | March 12 |
| First Square | April 20 |
| First Bloom | May 24 |
| 1st Glyphosate application (cutout, 0% open boll) | July 2 |
| First Open Boll | July 5 |
| 2nd Glyphosate application (10% Open Boll) | July 12 |
| First Pick | July 19 |
| Defoliant applied | July 23 |
| Second Pick | August 10 |

The lint yield and distribution between 1st and 2nd pickings is reported in Table 4.

TABLE 4

| | Total Yield | | | |
| --- | --- | --- | --- | --- |
| | Lint Yield (lbs/acre) | | | |
| Glyphosate Application Rate (g/ha) | 1st Pick | 2nd Pick | Total Yield | % from 1st Pick |
| ROUNDUP ® APPLIED AT 0% OPEN BOLL: | | | | |
| Control | 330 | 527 | 857 | 39.2 |
| 127.1 g/ha | 465 | 489 | 954 | 48.3 |
| 190.7 g/ha | 423 | 463 | 887 | 47.3 |
| 254.2 g/ha | 480 | 421 | 902 | 53.1 |
| ROUNDUP ® APPLIED AT 10% OPEN BOLL: | | | | |
| Control | 330 | 527 | 857 | 39.2 |
| 127.1 g/ha | 477 | 497 | 974 | 49.0 |
| 190.7 g/ha | 463 | 499 | 962 | 48.3 |
| 254.2 g/ha | 373 | 453 | 826 | 45.9 |

The effects of rate and timing of glyphosate applications on dry weight of regrowth per meter of row 31 days after final harvest or 41 days after glyphosate application are shown in Table 5. The application of glyphosate at 0% open boll resulted in less regrowth control at second and final harvest than applications made at 10% open boll regardless of the rate applied. The regrowth of treated plants is less than the untreated control plants.

TABLE 5

| Glyphosate application rate (g/ha) | Regrowth (g. of dry matter per meter of row) | | |
|---|---|---|---|
| | 0% Open Boll | 10% Open Boll | Average |
| Control | 7.6 | 7.6 | 7.6 |
| 127.1 | 4.1 | 2.9 | 3.5 |
| 190.7 | 2.5 | 1.9 | 2.2 |
| 254.2 | 2.0 | 1.4 | 1.7 |

The boll weights are reported in Table 6 for an average seed cotton weight of 25 boll samples from once and twice treated cotton plants. As seen from the results, treatment at all rates at 10% open boll did not have a meaningful impact on the lint yield. Most averages showed a slight increase in yield as a result of conditioning with glyphosate.

TABLE 6

| Glyphosate application rate (g/ha) | Boll Weight | | |
|---|---|---|---|
| | Once Treated | Twice Treated | Average |
| Boll Wt. (g) at First Harvest | | | |
| Control | 5.5 | 5.5 | 5.5 |
| 127.1 | 5.8 | 5.6 | 5.7 |
| 190.7 | 5.6 | 5.6 | 5.6 |
| 254.2 | 5.7 | 5.9 | 5.8 |
| Boll Wt. at Second Harvest | | | |
| Control | 5.2 | 5.2 | 5.2 |
| 127.1 | 5.4 | 5.4 | 5.4 |
| 190.7 | 5.3 | 5.2 | 5.3 |
| 254.2 | 5.1 | 5.0 | 5.1 |

Example 2

In this example, glyphosate was applied in two doses to Cultivar Delta Pine 5415 at rates within the range of 63.6–254.1 g/ha (0.25–1 pint/acre ROUNDUP ®) in combination with PHCA ®. The defoliant was the same as in example 1 with a second application of just DROPP ® at 22.7 g AI/acre. PHCA ® was applied at the rate of 0.3 gallons AI/acre. Table 7 shows the application timing and sequence.

TABLE 7

| Event Schedule | |
|---|---|
| Date of Planting | March 12 |
| First Square | May 28 |
| First Bloom | June 3 |
| First Open Boll | July 15 |
| 1st Glyphosate application (10% open boll) | July 20 |
| First Pick | August 1 |
| 2nd Glyphosate application (40% open boll) | August 2 |
| Defoliant applied | August 6 |
| Second Pick | August 16 |
| Regrowth Measured | September 15 |

TABLE 8

| Conditioner Application Rate | | Total Yield | | | |
|---|---|---|---|---|---|
| | | Lint Yield (lbs/Acre) | | | |
| Glyphosate (g/ha) | PHCA (g/ha) | 1st Pick | 2nd Pick | Total | % from 1st Pick |
| Control | | 390 | 726 | 1116 | 34.9 |
| 63.6 | 81.7 | 409 | 708 | 1117 | 36.6 |
| 127.1 | 81.7 | 388 | 584 | 972 | 39.0 |
| 190.7 | 81.7 | 465 | 496 | 961 | 47.9 |
| 127.1 | — | 469 | 593 | 1062 | 44.1 |
| 190.7 | — | 419 | 500 | 919 | 44.8 |

TABLE 8-continued

| Conditioner Application Rate | | Total Yield | | | |
|---|---|---|---|---|---|
| | | Lint Yield (lbs/Acre) | | | |
| Glyphosate (g/ha) | PHCA (g/ha) | 1st Pick | 2nd Pick | Total | % from 1st Pick |
| 254.2 | — | 489 | 382 | 870 | 55.8 |

The rate of glyphosate treatment at 10% open boll affected overall yield of this cultivar proportionally to the application rate although the addition of PHCA ® containing Krebs cycle acids increased yields at the same glyphosate application rate. The PHCA ® is mitigating the effects of the glyphosate on fruit production.

The affects of applying glyphosate at 10% and 40% open boll is shown in Table 9. Applying the glyphosate conditioner at 40% open significantly increased yield compared to treatment at 10 % open boll.

TABLE 9

| Glyphosate Application Rate (g/ha) | % Open Boll at Application | Yield v. % Open Boll | | | |
|---|---|---|---|---|---|
| | | Lint Yield (lbs/Acre) | | | |
| | | First | Second | Total | % First Pick |
| Control | | 419 | 669 | 1160 | 35.9 |
| 127.1 | 10% | 459 | 467 | 986 | 46.5 |
| 190.7 | 10% | 374 | 448 | 868 | 43.0 |
| 127.1 | 40% | 450 | 556 | 1176 | 45.7 |
| 190.7 | 40% | 537 | 603 | 1146 | 39.0 |

Table 10 reports the percent of plants with main stem terminal regrowth and dry weight of regrowth per meter of row as affected by glyphosate applications with and without PHCA ® containing Krebs acids at 10% open boll 30 days after final harvest or 57 days after glyphosate application. All treated plants showed acceptably low levels of regrowth with regrowth reducing as the amount of applied glyphosate increased.

TABLE 10

| Conditioner Application Rate | | Regrowth | |
|---|---|---|---|
| Glyphosate (g/ha) | PHCA ® (g/ha) | % Plants with Top Regrowth | Dry Weight of Regrowth (g dry matter/meter of row) |
| Control | | 24.9 | 13.2 |
| 63.6 | 81.7 | 4.7 | 2.0 |
| 127.1 | 81.7 | 5.1 | 1.0 |
| 190.7 | 81.7 | 0.8 | 0.3 |
| 127.1 | — | 5.1 | 1.0 |
| 190.7 | — | 0.0 | 0.1 |
| 254.2 | — | 0.0 | 0.1 |

Table 11 shows the effect on boll size of varying levels of glyphosate addition with and without PHCA ®. Sizes are calculated on an average of 25 random boll samples. The conditioning with PHCA ® resulted in higher boll sizes for the second harvest.

TABLE 11

| Conditioner Application Rate | | Boll Size | | |
|---|---|---|---|---|
| | | Boll Size (g) | | |
| Glyphosate (g/ha) | PHCA ® (g/ha) | 1st Pick | 2nd Pick | Average |
| Control | | 4.4 | 4.0 | 4.2 |
| 63.6 | 81.7 | 4.4 | 3.9 | 4.2 |
| 127.1 | 81.7 | 4.3 | 3.9 | 4.1 |
| 190.7 | 81.7 | 4.2 | 3.6 | 3.9 |
| 127.1 | — | 4.5 | 3.7 | 4.1 |
| 190.7 | — | 4.3 | 3.6 | 4.0 |

TABLE 11-continued

| Conditioner Application Rate | Boll Size | | |
|---|---|---|---|
| | | Boll Size (g) | |
| | 1st | | |
| Glyphosate (g/ha) PHCA ® (g/ha) | Pick | 2nd Pick | Average |
| 254.2 — | 4.3 | 3.3 | 3.8 |

Table 12 shows the beneficial impact on weevil infestation as a result of conditioning according to the invention. Conditioning according to the invention removed or eliminated squares and young bolls thus reducing the food supply for overwintering weevils and a lower level of infestation for beginning the following crop.

TABLE 12

| Conditioning Treatment | Number of Weevils/acre |
|---|---|
| Control | 1318.2 |
| 127.1 g/ha glyphosate | 401.5 |
| 190.7 g/ha glyphosate | 114.7 |
| 254.2 g/ha glyphosate | 57.2 |

The following examples are presented solely for the purposes of illustration. Nothing in the examples should be construed as limiting the scope of the appended claims.

I claim:

1. A process for preventing regrowth in cotton plants by a process comprising:
applying to cotton plant foliage at a time following first bloom within the range from about 0–50% open boll a conditioner comprising: (a) a regrowth inhibitor comprising glyphosate, sulfosate, or salts of either glyphosate or sulfosate in a sublethal amount sufficient to suppress vegetative regrowth after the conditioned plant is later chemically defoliated; and (b) a mixture of polyhydroxycarboxylic acids produced from the extraction of pentose-containing seed hulls and containing at least one acid of the Krebs acid cycle and a carbohydrate corresponding to said acid, wherein the acid in said mixture is applied in an amount within the range of about 1–10,000 grams per hectare.

2. A process as in claim 1 wherein the applying step comprises:
applying a conditioner containing glyphosate or a salt thereof to cotton plant foliage at a rate within the range of about 5 g/ha to about 1000 g/ha.

3. A process as in claim 1 wherein the applying step comprises:
applying a conditioner containing glyphosate or a salt thereof to cotton plant foliage at a rate within the range of about 75–500 g/ha.

4. A process as in claim 1 wherein the applying step comprises:
applying a conditioner containing glyphosate or a salt thereof to cotton plant foliage at a rate within the range of about 125–300 g/ha.

5. A process as in claim 1 wherein the applying step comprises:
applying a conditioner containing: (a) a sublethal amount of glyphosate, sulfosate, or salts of either glyphosate or sulfosate and (b) the extraction product from the extraction of pentosan-containing seed hulls, said extraction product containing a mixture of polyhydroxycarboxylic acids produced by the extraction of glucoxylane-based seed hulls.

6. A process as in claim 1 wherein the applying step comprises:
applying a conditioner containing: (a) a sublethal amount of glyphosate, sulfosate, or salts of either glyphosate or sulfosate and (b) a mixture of polyhydroxycarboxylic acids produced from the extraction of seed hulls, said conditioner being applied at a rate within the range from about 50–500 g/ha based on an active Krebs acid concentration.

7. A method as in claim 1 wherein the applying step comprises:
applying said conditioner at a time within the range from about 10–50% open boll.

8. A method as in claim 1 wherein the applying step comprises:
applying said conditioner at a time within the range from about 30–50% open boll.

9. A method as in claim 1 wherein the applying step comprises:
applying said conditioner at about 40% open boll.

10. A composition for preventing cotton regrowth, said composition comprising: (a) a regrowth inhibitor comprising glyphosate, sulfosate, or salts of either glyphosate or sulfosate in a sublethal amount sufficient to suppress vegetative regrowth after the conditioned plant is later chemically defoliated; and (b) a mixture of polyhydroxycarboxylic acids produced from the extraction of pentose-containing seed hulls and containing at least one acid of the Krebs cycle and a carbohydrate corresponding to said acid, wherein inhibitor and said mixture is present in a weight ratio of regrowth inhibitor to Krebs cycle acid at a ratio within the range from about 1:100 to about 100:1.

11. A composition as in claim 10 wherein said corresponding carbohydrate comprises hexoses and said composition comprising a weight ratio of regrowth inhibitor to Krebs acid component within the range of about 1:20 to about 20:1.

12. A composition as in claim 10 comprising a weight ratio of regrowth inhibitor to Krebs acid component within the range of about 1:3 to about 3:1.

* * * * *